US012779059B2

(12) United States Patent
Li et al.

(10) Patent No.: US 12,779,059 B2
(45) Date of Patent: Nov. 3, 2026

(54) BINDING PROTEIN TARGETING HER2, PREPARATION METHOD AND USE THEREOF

(71) Applicant: WEST CHINA HOSPITAL OF SICHUAN UNIVERSITY, Chengdu (CN)

(72) Inventors: Jiong Li, Chengdu (CN); Nongyu Huang, Chengdu (CN); Yang Cao, Chengdu (CN); Yuquan Wei, Chengdu (CN); Yang Zhang, Chengdu (CN)

(73) Assignee: WEST CHINA HOSPITAL OF SICHUAN UNIVERSITY, Chengdu (CN)

( * ) Notice: Subject to any disclaimer, the term of this patent is extended or adjusted under 35 U.S.C. 154(b) by 812 days.

(21) Appl. No.: 18/297,032

(22) Filed: Apr. 7, 2023

(65) Prior Publication Data

US 2023/0355814 A1 Nov. 9, 2023

Related U.S. Application Data

(63) Continuation of application No. PCT/CN2021/085321, filed on Apr. 2, 2021.

(30) Foreign Application Priority Data

Aug. 8, 2020 (CN) ........................ 202010792191.5

(51) Int. Cl.
*A61K 51/08* (2006.01)
*C07K 14/00* (2006.01)

(52) U.S. Cl.
CPC ............ *A61K 51/088* (2013.01); *C07K 14/00* (2013.01); *A61K 2123/00* (2013.01)

(58) Field of Classification Search
CPC ...... A61K 51/00; A61K 51/08; A61K 51/088; A61K 2123/00; C07K 14/00; C07K 2319/00; C12N 15/70
See application file for complete search history.

(56) References Cited

FOREIGN PATENT DOCUMENTS

| | | | |
|---|---|---|---|
| CN | 1816563 | A | 8/2006 |
| CN | 101270163 | A | 9/2008 |
| CN | 102100916 | A | 6/2011 |
| CN | 103290017 | A | 9/2013 |
| CN | 104262460 | A | 1/2015 |
| CN | 105085631 | A | 11/2015 |
| CN | 105087593 | A | 11/2015 |
| CN | 105198964 | A | 12/2015 |
| CN | 105693860 | A | 6/2016 |
| CN | 107082811 | A | 8/2017 |
| CN | 110944633 | A | 3/2020 |
| CN | 111592584 | A | 8/2020 |

OTHER PUBLICATIONS

Rejection Decision dated Jun. 13, 2022 received in corresponding patent family application No. 202010792191.5. English translation attached.
International Search Report dated Jun. 24, 2021 in International Application No. PCT/CN2021/085321. English translation attached.
First Office Action from corresponding Chinese Application No. 202010792191.5 , dated Sep. 29, 2021. English translation attached.
Second Office Action from corresponding Chinese Application No. 202010792191.5 dated Mar. 11, 2022. English translation attached.
Geng, L.L. et al. "Structure-based Design of Peptides with High Affinity and Specificity to HER2 Positive Tumors." Theranostics., vol. 5, No. 10, Aug. 1, 2015 (Aug. 1, 2015), pp. 1154-1165.
Eigenbrot, C. et al. "Structural Basis for High-affinity HER2 Receptor Binding by an Engineered Protein." Proc Natl Acad Sci USA., vol. 107, No. 34, Aug. 24, 2010 (Aug. 24, 2010), pp. 15039-15044.

*Primary Examiner* — D. L. Jones

(57) ABSTRACT

Provided are a binding protein targeting HER2, a preparation method and use thereof. The binding protein includes the following amino acid sequence (a): NDEMRX$_1$TYW X$_2$IALF X$_3$ X$_4$L X$_5$N X$_6$X$_7$KR X$_8$ X$_9$IR X$_{10}$LYDDP X$_{11}$X$_{12}$A X$_{13}$ X$_{14}$LEX$_{15}$ X$_{16}$A X$_{17}$LEA X$_{18}$ X$_{19}$ X$_{20}$. The binding protein can bind to HER2 and has an excellent affinity with HER2. A radionuclide molecular imaging probe may be prepared by means of nuclide labeling, and it can be used in the molecular imaging diagnosis and improve the tumor imaging diagnosis to a molecular level of specific expression of tumor cells, and the HER2 expression in possible tumor lesions in vivo can be monitored in real time before a treatment scheme is determined or in the process of monitoring a medicament treatment progress.

1 Claim, 7 Drawing Sheets

Specification includes a Sequence Listing.

SEQUENCE LISTING

```
Sequence total quantity: 5
SEQ ID NO: 1            moltype = AA  length = 58
FEATURE                 Location/Qualifiers
REGION                  1..58
                        note =         HER2          Seq1
source                  1..58
                        mol_type = protein
                        organism = synthetic construct
SEQUENCE: 1
AEAKYNDEMR ITYWEIALFA PLENEHKRAY IRRLYDDPSR ADELEEKAEL EAKAMAQG    58

SEQ ID NO: 2            moltype = AA  length = 58
FEATURE                 Location/Qualifiers
REGION                  1..58
                        note =         HER2          Seq2
source                  1..58
                        mol_type = protein
                        organism = synthetic construct
SEQUENCE: 2
AEAKYNEEMR ITYWAIALFA PLENEHKRAY IRRLYDDPSR ADELEEKAEL EAQAMAQG    58

SEQ ID NO: 3            moltype = AA  length = 58
FEATURE                 Location/Qualifiers
REGION                  1..58
                        note =         HER2          Seq3
source                  1..58
                        mol_type = protein
                        organism = synthetic construct
SEQUENCE: 3
AEAKYNDEMR ITYWHIALFA PLENEHKRAY IRRLYDDPSR ADELEEKARL EAKAMAQG    58

SEQ ID NO: 4            moltype = AA  length = 58
FEATURE                 Location/Qualifiers
REGION                  1..58
                        note =         HER2          Seq4
source                  1..58
                        mol_type = protein
```

-continued

```
                       organism = synthetic construct
SEQUENCE: 4
AEAKYNDEMR ITYWEIALFQ ALENEHKRAY IRRLYDDPSR ADELEEKAEL EAKAMAQG    58

SEQ ID NO: 5           moltype = AA  length = 58
FEATURE                Location/Qualifiers
REGION                 1..58
                       note =          HER2           Seq5
source                 1..58
                       mol_type = protein
                       organism = synthetic construct
SEQUENCE: 5
AEAKYNEEMR ITYWAIALFQ ALENEHKRAY IRRLYDDPSR ADELEEKAEL EAQAMAQG    58
```

BINDING PROTEIN TARGETING HER2, PREPARATION METHOD AND USE THEREOF

CROSS-REFERENCE OF RELATED APPLICATION

The present application is a continuation of the International Application No. PCT/CN2021/085321 filed on Apr. 2, 2021, which claims priority and benefit to a patent application No. 202010792191.5, filed on Aug. 8, 2020 to the China National Intellectual Property Administration, which is incorporated herein by reference in its entirety.

FIELD

The present disclosure relates to the technical field of immunology, and particularly, to a binding protein targeting human epidermal growth factor receptor 2 (HER2), and preparation method and use thereof.

BACKGROUND

The individualized and precise treatment of tumor-targeted therapeutic medicaments is currently an important issue worthy of attention in the field of tumor diagnosis and treatment. Human epithelial growth factor receptor-2 (HER2) is closely related to cell growth, activation, and sensitivity to chemoradiotherapy. HER2 monoclonal antibody therapy, represented by Trastuzumab and Pertuzumab, has significantly improved the prognosis of patients with HER2-positive breast cancer, and it is an important milestone in tumor molecular targeted therapy. The detection of HER2 expression and HER2 monitoring during disease progression are of great significance for targeted therapy, and the detection of HER2 expression in primary and metastatic lesions is the key to judge whether a breast cancer patient can be treated with HER2 as a target. Current detection methods include immunohistochemical detection for HER2 protein expression, and in situ hybridization detection for HER2 gene amplification, etc.

However, in the process of tumor treatment, the expression of HER2 may change, such that pathological examination cannot be carried out in time. Moreover, due to the inconsistency between tumor primary lesions and between primary lesions and metastatic lesions, pathological examination cannot evaluate the true situation of HER2 expression of possible tumor lesions in the whole body, resulting in certain one-sidedness. Second, some metastatic lesions are relatively small or deep, and it is difficult to obtain tumor lesion tissue sections. Therefore, there is an urgent clinical need for a real-time, non-invasive and specific molecular imaging monitoring method for HER2 in vivo. In addition, nuclide molecular imaging diagnosis performed for HER2 may measure changes in HER2 expression in multiple tumor lesions in the body before a treatment scheme is determined or in the process of monitoring a medicament treatment progress, so as to establish and adjust the treatment scheme.

At present, existing HER2 nuclide molecular imaging probes have entered clinical trials, e.g., nuclide-labeled whole immunoglobulins molecules and immunoglobulin fragments. Although monoclonal antibodies labeled with radionuclides, such as $^{89}$Zr-trastuzumab, may bind to HER2, they also lead to poor thermal stability, complex preparation process and other problems of such probes due to their slow clearance in the blood, low tissue penetration, great molecular mass, complex structure and other characteristics.

SUMMARY

Based on the problems existing in the relate art, an object of the present disclosure is to provide a binding protein targeting HER2. The binding protein targeting HER2 has the advantages of small molecular weight, stable structure, good tissue penetration and low cost, and it is thus suitable for the preparation of radionuclide molecular imaging probes.

Another object of the present disclosure is to provide a preparation method for a binding protein targeting HER2 and use thereof.

The present disclosure solves the technical problems with the following technical solutions.

The present disclosure provides a binding protein targeting HER2, the binding protein including the following amino acid sequence (a): NDEMRX$_1$TYW X$_2$IALF X$_3$ X$_4$L X$_5$N X$_6$X$_7$KR X$_8$ X$_9$IR X$_{10}$LYDDP X$_{11}$X$_{12}$A X$_{13}$ X$_{14}$LEX$_{15}$ X$_{16}$A X$_{17}$LEA X$_{18}$ X$_{19}$ X$_{20}$. Preferably, $X_1$ is E, D, T, S, Q, V, A, H, I, L, M, or R; $X_2$ is E, D, T, S, Q, V, A, H, I, L, M, or R; $X_3$ is A, G, T, S, Q, N, or V; $X_4$ is A, G, T, S, Q, V, or P; $X_5$ is E, T, S, Q, V, A, K, H, L, M, or R; $X_6$ is E, T, S, Q, V, A, K, H, I, L, M, or R; $X_7$ is E T, S, Q, V, D, K, H, I, L, M, or R; $X_8$ is A, T, S, Q, V, D, K, H, I, L, M, or R; $X_9$ is either Y or F; $X_{10}$ is E, D, T, S, Q, V, A, H, I, L, M, or R; $X_{11}$ is A, G, S, or T; $X_{12}$ is E, D, T, S, V, A, K, H, I, L, M, or R; $X_{13}$ is D, T, S, Q, V, A, K, H, I, L, M, or R; $X_{14}$ is E, T, S, Q, V, A, K, H, I, L, M, or R; $X_{15}$ is E, D, T, S, Q, V, A, H, I, L, M, or R; $X_{16}$ is E, D, T, S, Q, V, K, H, I, L, M, or R; $X_{17}$ is E, D, T, S, Q, V, A, H, I, L, M, or R; $X_{18}$ is E, D, T, S, Q, V, A, K, H, I, L, M, or R; $X_{19}$ is E, D, T, S, Q, V, A, K, H, I, L, M, or R; and $X_{20}$ is V, I, L, or M.

According to a preferred embodiment, the amino acid sequence of the binding protein further includes an amino acid sequence having at least 70% homology to the amino acid sequence (a). Preferably, the amino acid sequence of the binding protein further includes an amino acid sequence having at least 80% homology to the amino acid sequence (a). Preferably, the amino acid sequence of the binding protein further includes an amino acid sequence having at least 90% homology to the amino acid sequence (a). Preferably, the amino acid sequence of the binding protein further includes an amino acid sequence having at least 95% homology to the amino acid sequence (a).

According to a preferred embodiment, the amino acid sequence of the binding protein further includes an amino acid sequence obtained by substituting, deleting, or adding 1 to 10 amino acids in the amino acid sequence (a). Preferably, the amino acid sequence of the binding protein further includes an amino acid sequence obtained by substituting, deleting, or adding 1 to 8 amino acids in the amino acid sequence (a). Preferably, the amino acid sequence of the binding protein further includes an amino acid sequence obtained by substituting, deleting, or adding 1 to 5 amino acids in the amino acid sequence (a).

According to a preferred embodiment, the substituted, deleted, or added amino acids in the amino acid sequence (a) are not at at least one of positions 4, 5, 7, 8, 9, 11, 12, 13, 14, 17, 19, 22, 23, 26, 27, 30, 31, 32, 33, 36, 39, 40, 43, or 47 in the amino acid sequence (a).

According to an embodiment of the present disclosure, in the amino acid sequence (a) included in the binding protein, $X_1$ is I, L, M, or R; $X_2$ is E, A, H, I, L, M, or R; $X_3$ is A, S, Q, N, or V; $X_4$ is A, S, Q, V, or P; $X_5$ is E, T, S, Q, L, M, or R; $X_6$ is E, T, S, Q, L, M, or R; $X_7$ is H, I, L, M, or R;

$X_8$ is A, T, S, Q, M, or R; $X_9$ is either Y or F; $X_{10}$ is H, I, L, M, or R; $X_{11}$ is A, G S, or T; $X_{12}$ is H, I, L, M, or R; $X_{13}$ is D, T, S, Q, L, M, or R; $X_{14}$ is E, T, S, I, L, M or R; $X_{15}$ is E, D, I, L, M, or R; $X_{16}$ is Q, V, K, H, I, L, M, or R; $X_{17}$ is E, D, T, S, L, M, or R; $X_{18}$ is S, Q, V, A, K, M, or R; $X_{19}$ is V, A, K, H, M, or R; and $X_{20}$ is V, I, L, or M.

According to an embodiment of the present disclosure, in the amino acid sequence (a) included in the binding protein, $X_1$ is I; $X_2$ is E, A, or H; $X_3$ is A or Q; $X_4$ is A or P; $X_5$ is E; $X_6$ is E; $X_7$ is H; $X_8$ is A; $X_9$ is Y; $X_{10}$ is R; $X_{11}$ is S; $X_{12}$ is R; $X_{13}$ is D; $X_{14}$ is E; $X_{15}$ is E; $X_{16}$ is K; $X_{17}$ is E or R; $X_{18}$ is K; $X_{19}$ is A; and $X_{20}$ is M.

According to an embodiment of the present disclosure, the amino acid sequence included in the binding protein may be selected from the following amino acid sequences as set forth in SEQ ID NO: 1 to SEQ ID NO: 5.

```
                                         (SEQ ID NO: 1)
AEAKYNDEMRITYWEIALFAPLENEHKRAYIRRLYDDPSRADELEEKA

ELEAKAMAQG.

                                         (SEQ ID NO: 2)
AEAKYNEEMRITYWAIALFAPLENEHKRAYIRRLYDDPSRADELEEKA

ELEAQAMAQG.

                                         (SEQ ID NO: 3)
AEAKYNDEMRITYWHIALFAPLENEHKRAYIRRLYDDPSRADELEEKA

RLEAKAMAQG.

                                         (SEQ ID NO: 4)
AEAKYNDEMRITYWEIALFQALENEHKRAYIRRLYDDPSRADELEEKA

ELEAKAMAQG.

                                         (SEQ ID NO: 5)
AEAKYNEEMRITYWAIALFQALENEHKRAYIRRLYDDPSRADELEEKA

ELEAQAMAQG.
```

The present disclosure further provides a protein derivative capable of targeting HER2, the protein derivative being formed by an amino acid sequence obtained by substituting, deleting, or adding 1 to 10 amino acids in the amino acid sequence (a).

The present disclosure further provides a fusion protein, including a dimer or polymer formed by said binding proteins.

The present disclosure further provides a polynucleotide, encoding said binding protein.

The present disclosure further provides a derivative, which is a derivative formed by binding, conjugating, or labeling said binding protein.

The present disclosure further provides an expression vector, including said polynucleotide.

The present disclosure further provides a host cell, including said expression vector.

The present disclosure further provides a preparation method of a binding protein targeting HER2, the preparation method including: preparing DNA molecules encoding said binding protein; preparing an expression vector for the DNA molecules; introducing the expression vector into host cells; and expressing a target binding protein.

The present disclosure further provides use of said binding protein targeting HER2 in the preparation of a medicament or reagent for the diagnosis or treatment of a tumor. The medicament or reagent is a molecular imaging probe, and a developing preparation of the molecular imaging probe includes any one of a radionuclide, a radionuclide marker, or a molecular imaging preparation. The tumor includes a HER2-positive early-stage breast cancer, a HER2-positive metastatic breast cancer or a HER2-positive metastatic gastric cancer.

The present disclosure further provides a molecular imaging probe, including said binding protein and a developing preparation. The binding protein is conjugated to the developing preparation.

According to an embodiment of the present disclosure, the developing preparation is selected from any one of a radionuclide, a radionuclide marker, or a molecular imaging preparation; and optionally, the developing preparation is selected from $^{68}$Ga, $^{18}$F, or $^{99m}$Tc.

The present disclosure further provides a method for monitoring cancer progression. The method includes: a change in HER2 expression of a patient's tumor lesion in real time using said molecular imaging probe, to determine the cancer progression. The cancer includes a HER2-positive early-stage breast cancer, a HER2-positive metastatic breast cancer or a HER2-positive metastatic gastric cancer.

The present disclosure further provides use of said molecular imaging probe in the localization of a patient's diseased site. The patient is suspected of having a cancer associated with HER2 expression.

The present disclosure further provides use of said molecular imaging probe in the diagnosis of a cancer associated with HER2 expression.

The present disclosure further provides a method for diagnosing a cancer associated with HER2 expression. The method includes: administering said molecular imaging probe to a subject; and diagnosing, by means of molecular imaging diagnosis, whether the subject has the cancer associated with HER2 expression. The subject is suspected of having a HER2-positive early-stage breast cancer, a HER2-positive metastatic breast cancer or a HER2-positive metastatic gastric cancer.

The present disclosure further provides use of said molecular imaging probe in the monitoring of a medicament treatment progress of a patient. The patient has a HER2-positive early-stage breast cancer, a HER2-positive metastatic breast cancer or a HER2-positive metastatic gastric cancer.

The present disclosure further provides a clinical medication guidance method for a patient having a cancer. The method includes: comparing changes in HER2 expression of a tumor lesion of the patient before and after medication, to determine an effectiveness of a medicament; and performing clinical medication guidance. The cancer includes a HER2-positive early-stage breast cancer, a HER2-positive metastatic breast cancer or a HER2-positive metastatic gastric cancer.

The present disclosure further provides use of said molecular imaging probe in the screening of a medicament for the treatment of a cancer. The cancer includes a HER2-positive early-stage breast cancer, a HER2-positive metastatic breast cancer or a HER2-positive metastatic gastric cancer.

The present disclosure further provides a method for screening a medicament for the treatment of a cancer. The method including: administering a candidate medicament to a patient having a cancer associated with HER2 expression; comparing changes in HER2 expression in a tumor lesion of the patient before and after medication, to screen the medicament for the treatment of the cancer. The patient has a HER2-positive early-stage breast cancer, a HER2-positive metastatic breast cancer or a HER2-positive metastatic gastric cancer.

Based on the above technical solutions, the binding protein targeting HER2 provided by the present disclosure has at least the following technical effects.

The binding protein targeting HER2 provided by the embodiments of the present disclosure has the advantages of small molecular weight, stable structure, good tissue penetration, and low cost, and it is thus suitable for the preparation of radionuclide molecular imaging probes. The molecular probe prepared by nuclide labeling the binding protein of the present disclosure has the characteristics of small relative molecular weight, simple structure, single-stranded molecular structure, and strong thermal stability. In addition, the molecular probe also has high selectivity and affinity, as well as very low non-specific binding rate, and it can be quickly concentrated at a target site due to its strong tissue penetration, thereby obtaining high-contrast images within a short time after injection.

The binding protein is a protein backbone that can tolerate the insertion, deletion, or substitution of multiple amino acids whiling its folded and tertiary structure can be maintained unchanged. The binding protein has a main structure foundation with high stability and high solubility, and a protein sequence with a specific affinity interface can be designed by means of a computing method and screened and confirmed by means of a surface display technology. Compared with antibodies, the binding protein has more advantages, such as capability of maintaining the structural stability in an intracellular environment if no disulfide bond exists; high stability, facilitating various modifications; small molecular weight, generally 5 to 20 kDa, and good tissue penetration; good solubility; capability of being expressed in *E. coli* production; low production cost; and very great commercial value, etc. The HER2 binding protein coupled with a nuclide is prepared into a nuclide-labeled HER2 imaging probe, which may be rapidly concentrated at a HER2 expression site, thereby obtaining high-contrast images within a short time after injection. The binding protein targeting HER2 according to the present disclosure can bind to a human epidermal growth factor receptor 2 (HER2), and has good affinity with HER2. The binding protein according to the present disclosure may be prepared into a radionuclide molecular imaging probe by means of nuclide labeling, for performing molecular imaging diagnosis, which can improve the tumor imaging diagnosis to a molecular level of specific expression of tumor cells. In addition, the HER2 expression in possible tumor lesions in vivo can be monitored in real time before a treatment scheme is determined or in the process of monitoring a medicament treatment progress, thereby establishing and adjusting the treatment scheme. The binding protein can solve the problems such as poor blood and tissue permeability, poor stability, and high cost in the preparation of molecular image probes by radionuclide labeling of existing monoclonal antibodies. Therefore, the above-mentioned binding protein, as a new-generation molecular recognition tool, has broad application prospects in the diagnosis and treatment of diseases and other related biomedical fields.

BRIEF DESCRIPTION OF THE DRAWINGS

In order to clearly explain the technical solutions in the embodiments of the present application, the accompanying drawings required to be used in the description of the embodiments are briefly described below.

DETAILED DESCRIPTION

Figure 1:
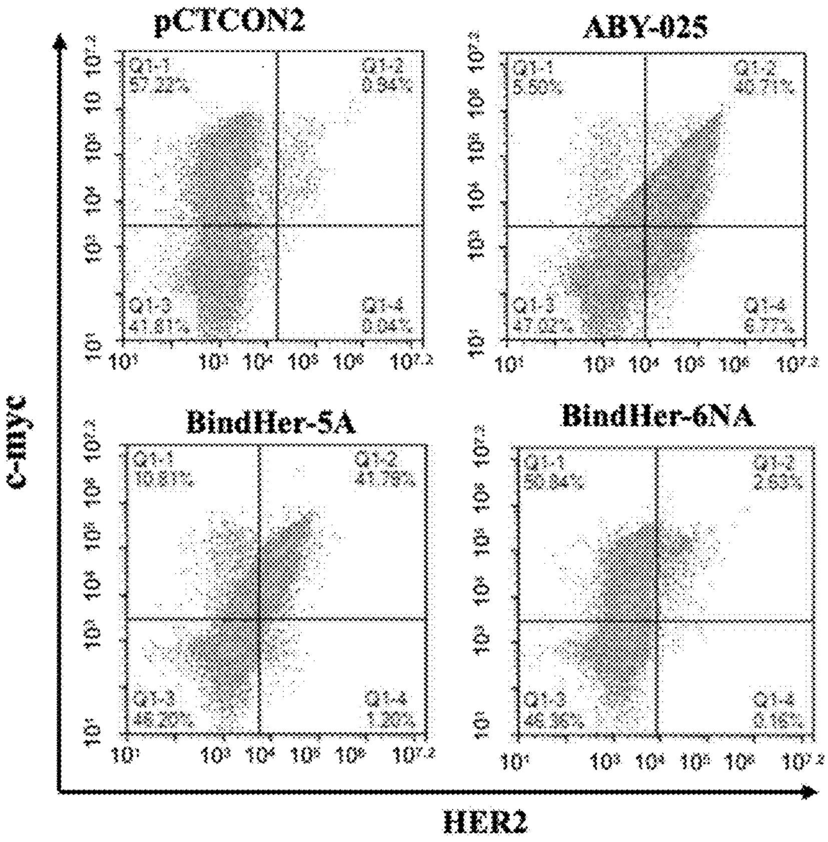
FIG. 1 is a diagram of flow cytometry analysis results of target proteins displayed on the surface of yeast in Example 2.

In order to clarify the objects, technical solutions and advantages of the present disclosure, the technical solutions of the present disclosure are clearly and thoroughly described below. Those technical solutions without specifying conditions in the following examples are usually carried out in accordance with conventional conditions or conditions suggested by manufacturers. The used reagents or instruments, the manufacturers of which are not specified, are conventional products that are commercially available.

The technical solutions of the present disclosure are described in detail below.

The present disclosure provides a binding protein targeting HER2, the binding protein including the following amino acid sequence (a): NDEMRX$_1$TYW X$_2$IALF X$_3$ X$_4$L X$_5$N X$_6$X$_7$KR X$_8$ X$_9$IR X$_{10}$LYDDP X$_{11}$X$_{12}$A X$_{13}$ X$_{14}$LEX$_{15}$ X$_{16}$A X$_{17}$LEA X$_{18}$ X$_{19}$ X$_{20}$. Preferably, X$_1$ is E, D, T, S, Q, V, A, H, I, L, M, or R; X$_2$ is E, D, T, S, Q, V, A, H, I, L, M, or R; X$_3$ is A, G, T, S, Q, N, or V; X$_4$ is A, G, T, S, Q, or P; X$_5$ is E, T, S, Q, V, A, K, H, I, L, M, or R; X$_6$ is E, T, S, Q, V, A, K, H, I, L, M, or R; X$_7$ is E, T, S, Q, V, D, K, H, L, M, or R; X$_8$ is A, T, S, Q, V, D, K, H, I, L, M, or R; X$_9$ is either Y or F; X$_{10}$ is E, D, T, S, Q, V, A, H, I, L, M, or R; X$_{11}$ is A, G, S, or T; X$_{12}$ is E, D, T, S, V, A, K, H, I, L, M, or R; X$_{13}$ is D, T, S, Q, V, A, K, H, I, L, M, or R; X$_{14}$ is E, T, S, Q, V, A, K, H I, L, M, or R; X$_{15}$ is E, D, T, S, Q, V, A, H, I, L, M, or R; X$_{16}$ is E, D, T, S, Q, V, K, H, I, L, M, or R; X$_{17}$ is E, D, T, S, Q, V, A, H, I, L, M, or R; X$_{18}$ is E, D, T, S, Q, V, A, K, H, I, L, M, or R; X$_{19}$ is E, D, T, S, Q, V, A, K, H, I, L, M, or R; and X$_{20}$ is V, I, L, or M.

Preferably, the amino acid sequence of the binding protein further includes an amino acid sequence having at least 70% homology to the amino acid sequence (a). Preferably, the amino acid sequence of the binding protein further includes an amino acid sequence having at least 80% homology to the amino acid sequence (a). Preferably, the amino acid sequence of the binding protein further includes an amino acid sequence having at least 90% homology to the amino acid sequence (a). Preferably, the amino acid sequence of the binding protein further includes an amino acid sequence having at least 95% homology to the amino acid sequence (a).

Preferably, the amino acid sequence of the binding protein further includes an amino acid sequence obtained by substituting, deleting, or adding 1 to 10 amino acids in the amino acid sequence (a). Preferably, the amino acid sequence of the binding protein further includes an amino acid sequence obtained by substituting, deleting, or adding 1 to 8 amino acids in the amino acid sequence (a). Preferably, the amino acid sequence of the binding protein further comprises an amino acid sequence obtained by substituting, deleting, or adding 1 to 5 amino acids in the amino acid sequence (a).

Preferably, the substituted, deleted, or added amino acids in the amino acid sequence (a) are not at Bind She least one of positions 4, 5, 7, 8, 9, 11, 12, 13, 14, 17, 19, 22, 23, 26, 27, 30, 31, 32, 33, 36, 39, 40, 43, or 47 in the amino acid sequence (a).

According to an embodiment of the present disclosure, in the amino acid sequence (a) includes in the binding protein, $X_1$ is I, L, M, or R; $X_2$ is E, A, H, I, L, M, or R; $X_3$ is A, S, Q, N, or V; $X_4$ is A, S, Q, V or P; $X_5$ is E, T, S, Q, L, M, or R; $X_6$ is E, T, S, Q, L, M, or R; $X_7$ is H, I, L, M, or R; $X_8$ is A, T, S, Q, M, or R; $X_9$ is either Y or F; $X_{10}$ is H, I, L, M, or R; $X_{11}$ is A, G, S, or T; $X_{12}$ is H, I, L, M, or R; $X_{13}$ is D, T, S, Q, L, M, or R; $X_{14}$ is E, T, S, I, L, M or R; $X_{15}$ is E, D, I, L, M, or R; $X_{16}$ is Q, V, K, H, I, L M, or R; $X_{17}$ is E, D T, S, L, M, or R; $X_{18}$ is S, Q, V, A, K, M, or R; $X_{19}$ is V, A, K, H, M, or R; and $X_{20}$ is V, I, L, or M.

According to an embodiment of the present disclosure, in the amino acid sequence (a) included in the binding protein, $X_1$ is I; $X_2$ is E, A, or H; $X_3$ is A or Q; $X_4$ is A or P; $X_5$ is E; $X_6$ is E; $X_7$ is H; $X_8$ is A; $X_9$ is Y; $X_{10}$ is R; $X_{11}$ is S; $X_{12}$ is R; $X_{13}$ is D; $X_{14}$ is E; $X_{15}$ is E; $X_{16}$ is K; $X_{17}$ is E or R; $X_{18}$ is K; $X_1$ is A; and $X_{20}$ is M.

The present disclosure further provides a protein derivative capable of targeting HER2, the protein derivative being formed by an amino acid sequence obtained by substituting, deleting, or adding 1 to 10 (e.g., 1, 2, 3, 4, 5, 6, 7, 8, 9, and 10) amino acids in the amino acid sequence (a).

The present disclosure further provides a fusion protein, including a dimer or polymer formed by said binding proteins.

The present disclosure further provides a polynucleotide, encoding said binding protein.

The present disclosure further provides a derivative, which is a derivative formed by binding, conjugating, or labeling said binding protein.

The present disclosure further provides an expression vector, including said polynucleotide.

The present disclosure further provides a host cell, including said expression vector.

The present disclosure further provides a preparation method of a binding protein targeting HER2, the preparation method including: preparing DNA molecules encoding said binding protein; preparing an expression vector for the DNA molecules; introducing the expression vector into host cells; and expressing a target binding protein.

The present disclosure further provides use of said binding protein targeting HER2 in the preparation of a medicament or reagent for the diagnosis or treatment of a tumor. The medicament or reagent is a molecular imaging probe, and a developing preparation of the molecular imaging probe includes any one of a radionuclide, a radionuclide marker, or a molecular imaging preparation. The tumor includes a HER2-positive early-stage breast cancer, a HER2-positive metastatic breast cancer or a HER2-positive metastatic gastric cancer.

The present disclosure further provides a molecular imaging probe, including said binding protein and a developing preparation. The binding protein is conjugated to the developing preparation.

According to an embodiment of the present disclosure, the developing preparation is selected from any one of a radionuclide, a radionuclide marker, or a molecular imaging preparation; and optionally, the developing preparation is selected from $^{68}$Ga, $^{18}$F, or $^{99m}$Tc.

The present disclosure further provides a method for monitoring cancer progression. The method includes: a change in HER2 expression of a patient's tumor lesion in real time using said molecular imaging probe, to determine the cancer progression. The cancer includes a HER2-positive early-stage breast cancer, a HER2-positive metastatic breast cancer or a HER2-positive metastatic gastric cancer.

The present disclosure further provides use of said molecular imaging probe in the localization of a patient's diseased site. The patient is suspected of having a cancer associated with HER2 expression.

The present disclosure further provides use of said molecular imaging probe in the diagnosis of a cancer associated with HER2 expression.

The present disclosure further provides a method for diagnosing a cancer associated with HER2 expression. The method includes: administering said molecular imaging probe to a subject; and diagnosing, by means of molecular imaging diagnosis, whether the subject has the cancer associated with HER2 expression. The subject is suspected of having a HER2-positive early-stage breast cancer, a HER2-positive metastatic breast cancer or a HER2-positive metastatic gastric cancer.

The present disclosure further provides use of said molecular imaging probe in the monitoring of a medicament treatment progress of a patient. The patient has a HER2-positive early-stage breast cancer, a HER2-positive metastatic breast cancer or a HER2-positive metastatic gastric cancer.

The present disclosure further provides a clinical medication guidance method for a patient having a cancer. The method includes: comparing changes in HER2 expression of a tumor lesion of the patient before and after medication, to determine an effectiveness of a medicament; and performing clinical medication guidance. The cancer includes a HER2-positive early-stage breast cancer, a HER2-positive metastatic breast cancer or a HER2-positive metastatic gastric cancer.

The present disclosure further provides use of said molecular imaging probe in the screening of a medicament for the treatment of a cancer. The cancer includes a HER2-positive early-stage breast cancer, a HER2-positive metastatic breast cancer or a HER2-positive metastatic gastric cancer.

The present disclosure further provides a method for screening a medicament for the treatment of a cancer. The method including: administering a candidate medicament to a patient having a cancer associated with HER2 expression; comparing changes in HER2 expression in a tumor lesion of the patient before and after medication, to screen the medicament for the treatment of the cancer. The patient has a HER2-positive early-stage breast cancer, a HER2-positive metastatic breast cancer or a HER2-positive metastatic gastric cancer.

In the present disclosure, the term "BindHer" refers to proteins targeting HER2. The present disclosure further provides use of said binding protein targeting HER2 in the preparation of a medicament or reagent for the diagnosis or treatment of a tumor. The medicament or reagent is a molecular imaging probe, and a developing preparation of the molecular imaging probe includes any one of a radionuclide, a radionuclide marker, or a molecular imaging preparation. The tumor includes a HER2-positive early-stage breast cancer, a HER2-positive metastatic breast cancer or a HER2-positive metastatic gastric cancer.

The features and performances of the present disclosure are further described in detail in conjunction with examples.

EXAMPLE

Example 1: Computer-Assisting Simulation and Design of Molecular HER2-Targeting Proteins Based on a complex structure of HER2 (PDB: 3WSQ) or HER2-ZHER2:342 (PDB: 3MZW), protein design was performed by means of Evodesign software. In the second step of the design process, i.e., Monte Carlo simulation, assuming that a main chain structure is fixed and amino acid sequences of less than 10 sites on a binding surface of protein interactions are fixed, more than 40 other amino acids are randomly arranged and combined, and sequences capable of being folded into a target three-dimensional structure were screened. In the sequences generated by Monte Carlo simulation, hundreds of low free energy protein sequences were calculated and screened out as candidate proteins based on an energy function. Through the dynamic adjustment of interface residues, the combinations of interface residues with very low binding free energy were searched. For the analysis of candidate protein sequences, the possibility that the immunogenicity returns to the protein design process was optimized by means of MHC linear epitope recognition and antibody epitope recognition. Based on the sequences (arrangement and combination features, surface hydrophilicity, and hydrophobic kernel analysis) and structural methods, the possibility of aggregation is investigated. At last, 11 preferred amino acid sequences are screened out.

Example 2: Screening of Binding Protein Targeting HER2

1. Target Proteins were Screen by Using Yeast Surface Display Technology.

1) Monoclonal yeast cells EBY100 were revived and picked into 5 mL of YPD medium, and cultured overnight at 30° C. at 220 rpm.

2) 100 μl of yeast medium was pipetted into 5 mL of fresh YPD medium, and cultured overnight at 30° C. at 220 rpm;

3) OD600 was measured on the next day, the yeast was diluted to OD600=0.2 with the fresh YPD medium, and further cultured at 30° C. for about 4 h until OD600=1.0 to 1.5;

4) The yeasts were collected in a 50 ml centrifuge tube, centrifuged at 4° C., 2000 g for 5 min; a supernatant was discarded; 25 ml of pre-cooled sterile water was added; the yeasts were resuspended with a vortexer, centrifuged at 4° C. 2000 g for 5 min, and the supernatant was discarded.

5) 5 ml of pre-cooled 0.1 M lithium acetate, which was filtered and sterilized, was added, followed by resuspending with the vortexer and centrifuging at 4° C., 2000 g for 5 min.

6) The supernatant was discarded, 200 μl of pre-cooled 0.1 M lithium acetate was added, the precipitate was resuspended and then placed on ice, aliquoting into sterilized EP tubes with 100 μl of resuspension solution per tube.

7) Centrifugation was performed at 4° C., 2000 g for 5 min, the supernatant was carefully removed by pipetting, and 10 μl of salmon essence single-stranded DNA (boiled for 5 min and placed on ice for 2 min), 1 μg of plasmids, and 500 μl of yeast treatment solution (10 mM Tris PH=7.5, 100 nM lithium acetate, 0.4 mM EDTA, 40% PEG3350(w/v)) were added, followed by resuspending with the vortexer for well mixing.

8) The resuspension solution was cultured statically at 30° C. for 30 min, followed by performing heat shock at 42° C. for 20 min, and placing on ice for 2 min.

9) Centrifugation was performed at 2000 g for 5 min, the supernatant was discarded, 1 ml of YPD medium was added, and cultured at 30° C. with shaking for 1 to 2 h;

10) Centrifugation was performed at 2000 g for 5 min, 1 ml of SDCAA medium was added and resuspended to obtain a resuspended product, 10 μl of the resuspended product was pipetted into 90 μl YPD, applying into a SDCAA plate, and a conversion rate was checked. 10 μl of bacterial solution was additionally pipetted into a liquid medium containing 5 ml of SDCAA, and cultured overnight at 30° C. at 220 rpm for flow cytometry.

2. the Targeting Ability was Detected by Means of Flow Cytometry.

1) OD value was measured on the next morning, 10 OD bacteria were pipetted and centrifuged at 2000 g for 5 min, and the supernatant was discarded; the cells were resuspended in 10 mL of fresh SDCAA medium until the OD reached 1, cultured at 30° C. till the OD reached 2 to 5, which was a logarithmic phase of yeasts.

2) The yeast cells of 10 OD were pipetted and centrifuged at 900 g for 5 min, the supernatant was discarded, the cells were resuspended in 10 ml of SGCAA medium to allow the OD value to reach 1, and induced at 20° C. with shaking for 18 to 24 h.

3) The corresponding volume of yeast cells was pipetted according to an amount of $10^7$/tube, centrifuged at 2000 g for 5 min, the supernatant was removed by pipetting, 5 ml of sterile PBS was added and mixed well, centrifuged at 2000 g for 5 min, the supernatant was removed by pipetting, 1 ml of sterile PBS was added for resuspending, followed by aliquoting into flow tubes.

4) Centrifugation was performed at 2,000 g for 5 min, the supernatant was discarded, and 100 μl of liquid was left to resuspend the yeast thoroughly; Anti-cmyc was added at 0.5 μl/tube, and HER2-biotin was added at 1 μl/tube, followed by incubating in a shaker at room temperature for 30 min to ensure that the cells were in a suspended state.

5) Centrifugation was performed at 4° C., 12,000 g for 30 s, the supernatant was removed by pipetting, 2 ml of pre-cooled PBS was added per tube, followed by resuspending and centrifuging, the cells were precipitated, 100 μl of pre-cooled PBS was added for resuspending, and then secondary antibodies were incubated: Goat Anti-Chicken IgG Antibody-Alexa Fluor 647 (1:100 in dilution, 1 µl/tube), Streptavidin-Alexa Fluor 488 (1:100 in dilution, 1 µl/tube).

6) The resuspended cells were incubated on ice in the dark for 15 mm, and then centrifuged, and the supernatant was discarded; 2 ml of pre-cooled PBS was added for resuspending and then centrifuged, and the supernatant was discarded.
7) 500 µl of 1% paraformaldehyde was added per tube, mixed well, kept at 4° C. for 30 min, followed by centrifuging and discarding the supernatant; 2 ml of pre-cooled PBS was added per tube to wash twice, and then 0.3 ml of pre-cooled PBS was added to fully resuspend the yeasts. The test samples were loaded on the machine.

Results in FIG. 1 indicate that computer-designed base sequences are inserted respectively between NheI and BamhI restriction cleavage sites in an expression vector pCTcon2 of yeast surface display. The yeast surface display is detected by means of flow cytometry, and 5 sequences have amino acid sequences targeting HER2.

The amino acid sequences having the capability of targeting HER2 respectively include:

```
amino acid sequence of artificially bound
protein Seq11:
                                    (SEQ ID NO: 1)
AEAKYNDEMRITYWEIALFAPLENEHKRAYIRRLYDDPSRADELEEKA

ELEAKAMAQG;

amino acid sequence of artificially bound
protein Seq2:
                                    (SEQ ID NO: 2)
AEAKYNEEMRITYWAIALFAPLENEHKRAYIRRLYDDPSRADELEEKA

ELEAQAMAQG;

amino acid sequence of artificially bound
protein Seq3:
                                    (SEQ ID NO: 3)
AEAKYNDEMRITYWHIALFAPLENEHKRAYIRRLYDDPSRADELEEKA

RLEAKAMAQG;

amino acid sequence of artificially bound
protein Seq4:
                                    (SEQ ID NO: 4)
AEAKYNDEMRITYWEIALFQALENEHKRAYIRRLYDDPSRADELEEKA

ELEAKAMAQG;
and

amino acid sequence of artificially bound
protein Seq5:
                                    (SEQ ID NO: 5)
AEAKYNEEMRITYWAIALFQALENEHKRAYIRRLYDDPSRADELEEKA

ELEAQAMAQG.
```

Example 3

This example relates to a preparation method for a binding protein targeting HER2 (BindHer).

1. Gene Synthesis and Cloning Construction of BindHer Molecules

Gene synthesis was performed based on the amino acid sequences of the binding proteins obtained in Example 2 and having the capability of targeting HER2. Cysteine was introduced at a carboxyl end of BindHer to facilitate radionuclide labeling. For the convenience of expression, BindShe plasmids were subcloned into a pET29a vector to construct pET29a-BindShe plasmids. The plasmids were validated by enzyme digestion and sequenced using an automated sequencer. After it was validated that the vector had been successfully constructed, the vector was transformed into an *E. coli* BL21(DE3) expression strain.

2. Expression and Purification of Recombinant Protein

Monoclonal bacteria of *E. coli* BL21(DE3) containing pET29a-BindHer expression plasmids were inoculated into a kanamycin-containing LB liquid medium, cultured at 37° C. until an optical density (OD600 nm) reached 0.6 to 0.8; 0.1 µM of IPTG was added, induced overnight at 18° C.; a culture was collected by centrifugation (4500 rpm, 20 min), and the bacteria were collected and stored at −20° C.

The bacteria were suspended according to a volume ratio of wet bacteria to buffer (20 mM PB, 500 mM NaCl, pH 8.0) of 1:10, followed by performing ultrasonication for 30 min. After the ultrasonication of cells, the cells were centrifuged at 13,000 rpm for 30 min at 4° C., and the supernatant was collected; crude purification was performed on the supernatant by using 30 ml of affinity chromatography filler Chelating Sepharose™ Fast Flow (GE Healthcare Life Sciences, Sweden), desalt; and then further purification was performed by using cation exchange SP Sepharose™ Fast Flow (GE Healthcare Life Sciences, Sweden). The molecular weights thereof were analyzed by means of reduced SDS-polyacrylamide gel electrophoresis; and the purity was analyzed by means of non-reduced SDS-polyacrylamide gel electrophoresis and reversed-phase high performance liquid chromatography (RP-HPLC).

Figure 2:
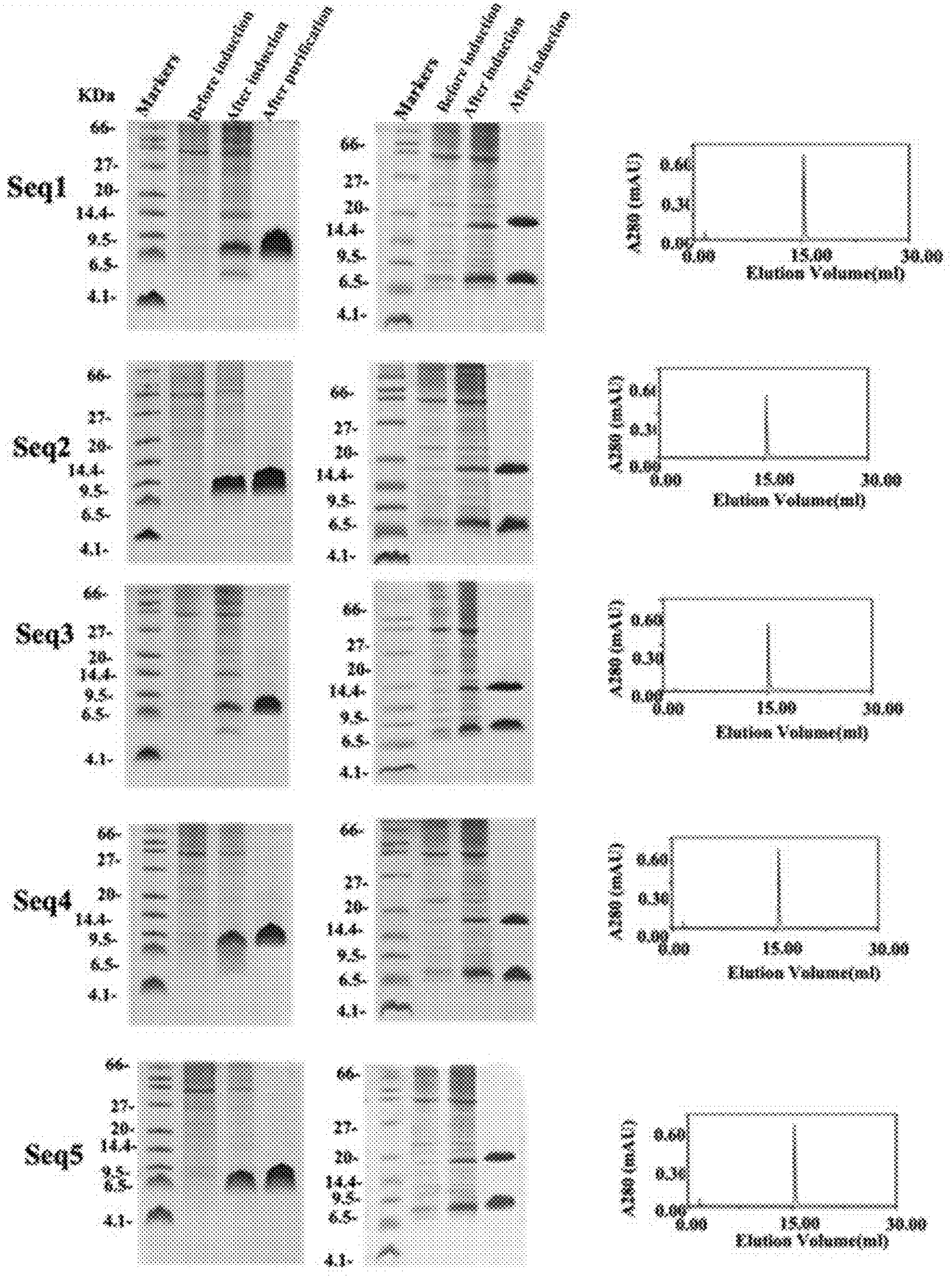
FIG. 2 is a diagram of SDS-PAGE electrophoresis analysis and reversed-phase high-performance liquid phase analysis of BindHer after expression and purification in Example 3.

The results are shown in FIG. 2. A BindShe protein having a molecular weight in consistent with a theoretical value and high purity can be obtained by expressing and purifying an expression vector constructed by gene cloning. As shown in leftmost column of FIG. 2, the molecular weight of BindHer protein, detected by reduced SDS-polyacrylamide gel electrophoresis, is consistent with the theoretical molecular weight. The middle column of FIG. 2 indicates that the BindHer protein has monomers and dimers as analyzed by non-reduced SDS-polyacrylamide gel electrophoresis. The rightmost column of FIG. 2 reveals that the purity of the BindHer protein is greater than 95% as analyzed by reversed-phase high-performance liquid chromatography.

Example 4

The affinity of BindHer for a HER2 protein is detected in this example.

The interactions between BindHer protein and HER2 was analyzed by means of surface plasmon resonance on a Biacore™ T200 system (GE Healthcare, USA).

1) A recombinant HER2 extracellular domain (HER2-ECD) was fixed on a surface of a CM5 chip (amine coupling method). A HER2-ECD protein (10004-HCCH, Sino Biological Inc., Beijing, China) was coupled by amines of a carboxylated dextran layer on the surface of a CM5 sensing chip (BR-1000-12, GE Healthcare, USA).
   a) Dextran surface activation: 0.4 M of N-ethyl-N'-(3-dimethylaminopropyl) carbodiimide and 0.1 M of N-hydroxysuccinimide were mixed in a ratio of 1:1 (vol/vol), running at a flow rate of 10 µL/min for 10 min.
   b) HER2-ECD binding: 50 µg/mL HER2-ECD was taken and dissolved in a buffer of 10 mM acetic acid with pH of 4.5, running at a flow rate of 10 µL/min for 5 min.
   c) The unbound HER2-ECD: 1 M of ethanolamine was removed, with pH of 8.5, running at a flow rate of 10 µL/min for 10 min, and the unbound HER2-ECD was removed. The signal of HER2 bound to the CM5 surface was approximately 2000 response units.

2) Affinity detection a) The protein to be detected was diluted with a buffer of 10 mM of HEPES and 150 mM of NaCl, with pH of 7.4, into different concentrations, and for each concentration, 10 μL/min was injected in 3 min; and then the system was equilibrated at 10 μL/min for 10 min.

b) Surface regeneration: 10 mM HCl with pH of 2.0, running at 10 μL/min for 2 min.

3) Data processing:

A diagram was obtained by subtracting reference channel from the diagram obtained after the test samples arrived in the detection channel, reference correction was performed, and the obtained curve was described by using a 1:1 Lamgmuir model to fit a kinetic model. The Bia-evaluation analysis software was used for data processing, and the affinity kinetics of the test samples were calculated.

Figure 3:
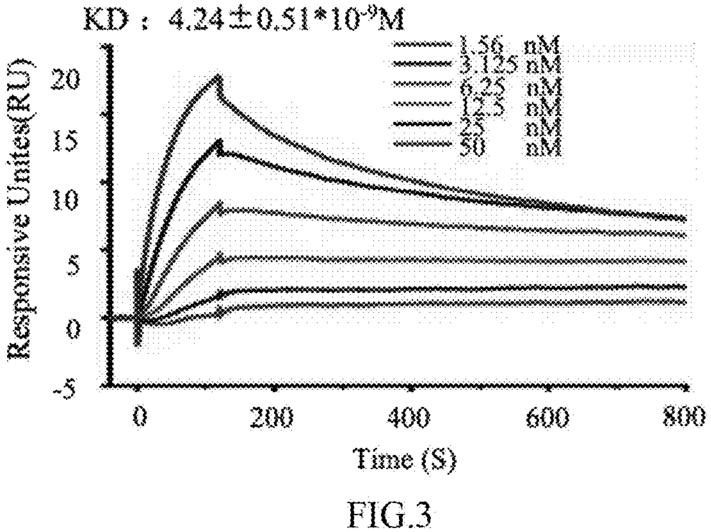
FIG. 3 is a diagram of a detection of an interaction between a HER2 extracellular domain protein and a BindShe protein using an SPR technology in Example 4.

The results are shown in FIG. 3. The protein was fitted by the intermolecular interactions of a 1:1 binding model, and the kinetic constants (dissociation rate constant (kd) and binding rate constant (ka)) and equilibrium constants KD as well as induction diagram of the binding between the BindHer protein and Her2 are obtained and shown in FIG. 3. The results indicate that the affinity (KD) of BindHer is $4.24\pm0.51\times10^{-9}$M.

Example 5

In the present example, the BindHer protein targets HER2-positive cells.

1. Fluorescent Labeling of BindHer Protein

1) Preparation of fluorescein: 4.273 mg of fluorescein-5-maleimide (62245, Thermo Fisher Scientific) was accurately weighed, 0.8 ml of DMSO was added for completely dissolving, and then the volume was adjusted to 1 ml, i.e., reaching a concentration of 10 mM, and the solution was stored in the dark.

2) Pretreatment of protein: 1M TECP solution and BindHer protein solution were mixed well and then placed at room temperature for 1 h, and the final concentration of TECP was 10 mM; TECP was desalted and removed using NAP-5 (17085302, GE Healthcare) pre-equilibrated with 20 mM sodium phosphate, 150 mM NaCl, and pH 7.0 buffer, and a concentration was measured.

3) Fluorescein-5-maleimide was added into the reaction system of BindHer protein at a molar amount of the fluorescein-5-maleimide to sulfhydryl groups to be coupled of 25:1, mixed well, and placed at room temperature for 2 h or overnight at 4° C. in the dark.

4) The free fluorescein was desalted to remove with NAP-5 pre-equilibrated with 20 mM phosphate, 150 mM NaCl, and pH 7.0 buffer.

5) Absorbance values were detected at wavelengths of 280 nm and 495 nm, respectively, and a fluorescent labeling rate and a protein concentration were calculated.

2. Flow Cytometry Analysis of Targeted Binding

Conventionally HER2-positive cell lines SK-BR3 and BT474, and a negative cell line MDA-MB-231 were cultured. The cells in the logarithmic growth phase were collected by pancreatic digestion, washed with PBS three times. The cell suspension density was adjusted with PBS to $2\times10^{6}$/ml, and 100 μl of each cell line was added into corresponding flow tubes. 100 μl of fluorescently labeled BindHer protein (100 nM) was added, incubated for 30 mM at room temperature. For a blocking group, 100-fold unlabeled BindShe protein was added prior to adding the fluorescently labeled BindShe protein, and incubated at 37° C. for 1 h. 3 ml of PBS was added and washed three times at 1500 rpm for 5 min. 300 μl of PBS was added at last. 10,000 cells were collected for loading on the machine, and detected at an excitation wavelength of 488 nm.

Figure 4:
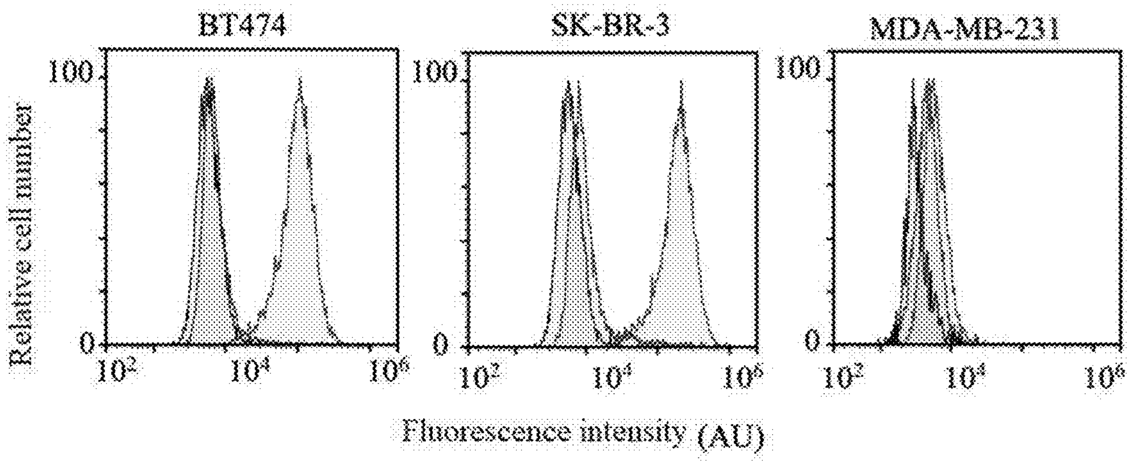
FIG. 4 illustrates binding rates of BindHer protein targeting HER2-positive cells analyzed by means of flow cytometry in Example 5.

The results are shown in FIG. 4. As shown in FIG. 4, three human breast cancer cells, i.e., BT474 (HER2+), SK-BR-3 (HER2+) and MDA-MB-231 (HER2−), are used for flow cytometry analysis of BindHer protein molecular fluorescent probes, and their specific binding to cells is investigated based on fluorescence shift.

In the Her2-positive cell line BT474 and SK-BR-3 cells, BindHer has an enhanced average fluorescence intensity relative to a blank control group and the blocking group, while the average fluorescence intensity is not enhanced in the Her2-negative cell line MDA-MB-231. It indicates that the binding effect of this probe against the HER2-positive cell lines depends on the binding specificity of BindShe molecules.

All the fluorescence signals of the BindHer protein molecular fluorescent probe binding to MDA-MB-231 cells are weak, indicating that the fluorescent labeled BindHer cannot specifically bind to HER2-negative MDA-MB-231 cells.

In summary, the BindHer protein fluorescent probes can specifically bind to BT474 and SK-BR-3 cells that highly express HER2, but unable to specifically bind to MDA-MB-231 cells serving as HER2-negative control.

Example 6

The thermal stability was analyzed in this example.

The samples were heated at 100° C. for 1 h, the detection was performed on a circular chromatograph (Aviv Model 400, Aviv Biomedical Inc., USA), and each sample and PBS control were detected in sequence, with setting parameters: temperature of 25° C., scanning wavelength ranging from 195 nm to 260 nm, and optical diameter of 2 mm.

Figure 5:
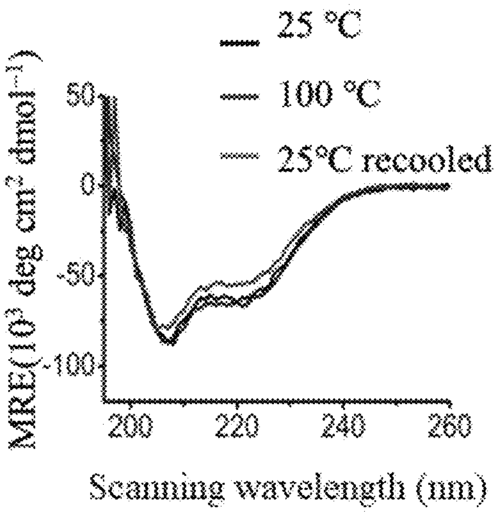
FIG. 5 is a heat stability analysis diagram of a BindHer protein in Example 6.

The results are shown in FIG. 5. A secondary structure of the BindHer protein at room temperature is characterized by a strong positive peak at 195 nm, two negative characteristic shoulder peak bands respectively at 222 nm and 208 nm, and a weak positive peak at 216 nm. The peak shape is intact as shown in FIG. 5. The results indicate that the BindHer protein has a secondary structure between an a-helix and a random coil. The results of the thermal stability experiment indicate that the molar ovality of BindHer is not significantly changed when heated at 100° C. for 1 h, indicating good thermal stability.

Example 7

The preparation of a $^{99m}$Tc-BindHer molecular probe and effects of specific binding to Her2 tumor exhibited in PET/CT imaging in a nude mouse with a HER2-positive cell transplant tumor are described in this example.

1. Preparation of $^{99m}$Tc-BindHer Molecular Probe

10 μl of sodium gluconate (1.28 mol/L), 10 μl of EDTA (0.25 mol/L, pH 8.0), 10 μl of stannous chloride (5.6 mg/ml, prepared with 5% dilute hydrochloric acid), and 70 μl of BindHer protein (100 μg) were added into a labeling tube in sequence, and 100 μl of $^{99m}$TcO4-solution (about 50 MBq) was added and mixed well, and incubated for 20 min at room temperature.

2. Detection of Labeling Rate

With instant thin-layer chromatography-silica gel (iTLC-SG, SG10001), Rf of $^{99m}$TcO4 was 1, and Rf of $^{99m}$Tc colloidal and Rf of technetium-labeled protein were 0, when using PBS as an developing agent; Rf of $^{99m}$TcO4- and Rf of technetium-labeled protein were 1, and Rf of $^{99m}$Tc colloidal was 0, when using a developing agent of pyridine: glacial acetic acid:water=10:6:3. 1 μl of sample was taken and applied on a thin layer plate to generally form a dot. A distance between a baseline of sample application and a bottom edge was 1.0 to 1.5 cm, and a diameter of the sample dot was generally no more than 2 mm. The thin layer plate applied with the samples was placed into a small beaker with a developing agent. A depth of immersion into the developing agent was 5 mm from the origin. The beaker was sealed with a tin foil, and the thin layer plate was taken out when developing to a specified distance (generally 8 to 15 cm), and scanned with a y scanner to detect a radiological purity. The radiological purity of the $^{99m}$Tc-BindHer molecular probe was 98.4±0.38%.

3. SPECT/CT Imaging:

Female nude mice aged 4 to 6 weeks were purchased from Beijing Huafukang Biotechnology Company, and raised in an SPF nude mouse room of our laboratory animal center. The HER2-positive cell line SK-BR-3 and the HER2-negative cell line MDA-MB-231 were cultured conventionally. The SK-BR-3 cells in the logarithmic growth phase were collected by pancreatic digestion, washed with PBS three times, a density of a cell suspension was adjusted with PBS, and the right axilla of the nude mice were inoculated with the cell suspension at $1\times10^7$ cells/0.2 ml per mouse. The diet and mental state of each of the tumor-bearing nude mice was observed every day, and tumor size (volume V=π/6× tumor growth×tumor width$^2$) and the body weight of each nude mouse were measured every three days. The tumors were ready for the experiment when the volume thereof reached 80 to 100 mm$^3$.

$^{99m}$Tc-BindHer molecular probe (1 MBq, 1 nM) was injected into SK-BR-3 and MDA-MB-231 tumor mice (n=4) through tail veins, and animal image development was performed using single photon emission computed tomography (SPECT/CT) imaging instrument equipped with a pinhole collimator at 1, 2, 4 and 8 h after injection of a developer. All tumor-bearing mice were anesthetized with isoflurane prior to the development, and were allowed to lie prostrate on an examination table. Parameters were collected: a magnification of 3.2, a collection matrix of 256×256, and collection time of 20 min.

In a blocking experiment, $^{99m}$Tc-BindHer was injected together with 80 μg of unlabeled $^{99m}$Tc-BindHer into SK-BR-3 tumor-bearing mice (n=4) through the tail veins, followed by the developing as described above.

Image analysis was performed by means of Vivo-Scope Brower software. Positions of the tumor, heart, brain, lung, liver, kidney, muscle, bone, and bladder were determined according to CT positioning during the image analysis. The cross-section of the visceral organ was manually drawn to obtain the radioactivity count per unit volume. T/NT was calculated.

4. Statistical Processing:

Statistical processing was performed using Graph Pad Prim8.0 statistical software. The measurement data satisfying the normal distribution were expressed in the form of x±s, and one-way analysis of variance was used to compare T/NT before blocking, after blocking, and HER2 negative, with difference P<0.05 indicating statistically significance.

Figure 6A:
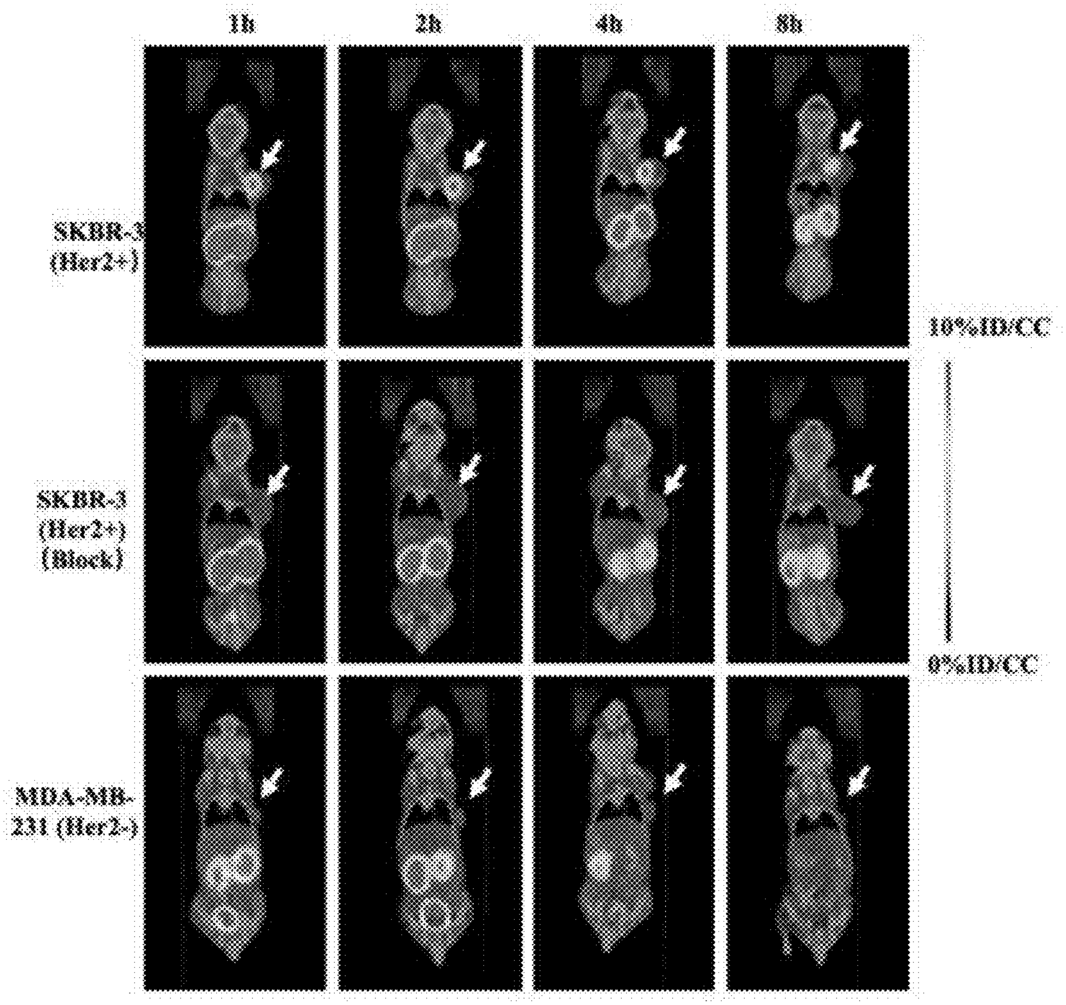
FIGS. 6*a* and 6*b* show a SPECT/CT developing diagram of a molecular probe of a $^{99m}$Tc-labeled BindHer protein in a transplant model of a nude mouse with a breast cancer in Example 7.
Figure 6B:
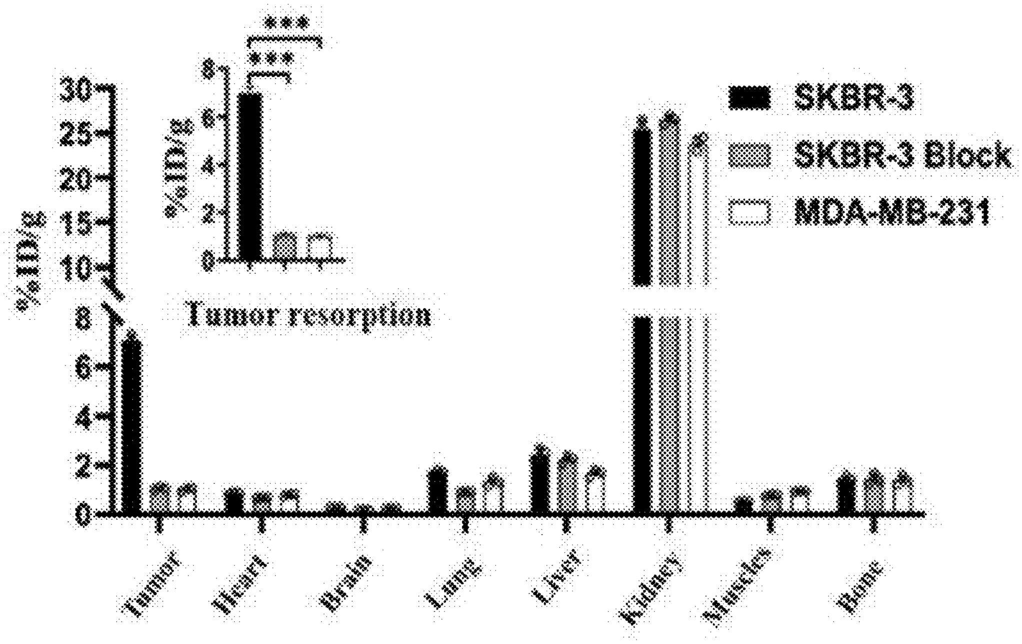

The results are shown in FIGS. 6*a* and 6*b*. As shown in FIG. 6*a*, the images developed at 1 h, 2 h, 4 h, and 8 h after injection of $^{99m}$Tc-BindHer exhibit tumor targeting specificity (see radioactive concentration) (indicated by an arrow) at the tumor site; the image developed at 1 h, 2 h, 4 h, and 8 h after BindHer blocking exhibit no radioactive concentration at the tumor site (indicated by an arrow); and the images developed at 1 h, 2 h, 4 h, and 8 h after injection of $^{99m}$Tc-BindHer to Her2-negative breast cancer-transplanted mice exhibit no radioactive concentration at the tumor site (indicated by an arrow). $^{99m}$Tc-BindHer was injected into the tumor nude mice subcutaneously transplanted with breast cancer cells SKBR-3 for SPECT/CT imaging. The results indicate that tumors of tumor-bearing mice have targeted absorption and have a high tumor/normal tissue ratio, and a tumor-liver ratio of $^{99m}$Tc-BindHer is 9.1 in 4 h after the injection. Radioactive absorption at all time points in the tumor is higher than all other organs except the kidney and bladder (as shown in FIG. 6*b*). After blocking SKBR-3 subcutaneous transplanted tumor nude mice with excessive unlabeled BindHer protein, the tumor absorbed $^{99m}$Tc-BindHer is significantly reduced, without affecting the absorption of other organs. The developed images of the tumor nude mice model subcutaneously transplanted with breast cancer cells MDA-MB-231 and injected with $^{99m}$Tc-BindHer indicate that the tumor radioactivity absorption is not obvious.

Example 8

The preparation of a $^{68}$Ga-BindHer molecular probe and effects specific binding to Her2 tumor exhibited in PET/CT imaging in a nude mouse with a HER2-positive cell transplant tumor are described in this example.

1. Preparation of $^{68}$Ga-BindHer Molecular Probe:

(1) Pretreatment of protein: TCEP was added to BindHer (3 mg/mL) in a ratio of 1 mM TCEP to 1 mg of protein and mixed well, and the mixture was placed at room temperature for 30 min. Then, solution replacement was performed using a NAP-5 (17-0853-01, GE Healthcare, USA) desalting column to replace the protein into a PBS solution while removing TCEP.

2) Coupling reaction of solution protein and NOTA: a protein and a chelating agent were added to 50 mg/mL MMA-NOTA (B-622, Macrocyclics, USA) according to a molar ratio of the protein to the chelating agent of 1:3, and mixed well, and then the mixture was placed at room temperature overnight for reaction. Free MAL-NOTA was removed using the NAP-5 column according to the above loading and collection rules. The BindHer-NOTA sample was replaced into a 0.1 M, pH 4.0 sodium acetate solution (3) $^{68}$Ga labeling of BindHer-NOTA: 100 μL of precursor protein BindHer-NOTA (a buffer was a 0.1M, pH 4.0 sodium acetate solution, in which the precursor protein concentration was adjusted to 2 mg/mL) was added with 100 μL of pre-buffered $^{68}$Ga solution (about 10 MBq) and mixed well, and the mixture was incubated at 75° C. for 15 min. Solution displacement was performed with a NAP-5 desalting column, and $^{68}$Ga-BindHer was replaced into the PBS solution while removing free $^{68}$Ga. The purify was performed with TLC, and the purity of the $^{68}$Ga-BindHer molecular probe was 98.21±0.52%.

2. In Vivo PET/CT Imaging

An animal tumor model was established in the same manner as described in Example 5. 10 μg (about 1.5 MBq/mouse, diluted to 100 μL with normal saline) of $^{68}$Ga- BindHer molecular probe was injected into the breast cancer-bearing mice through the tail veins, and a PET/CT imaging instrument was used for dynamic imaging of the animals after injecting a developer.

Figure 7A:
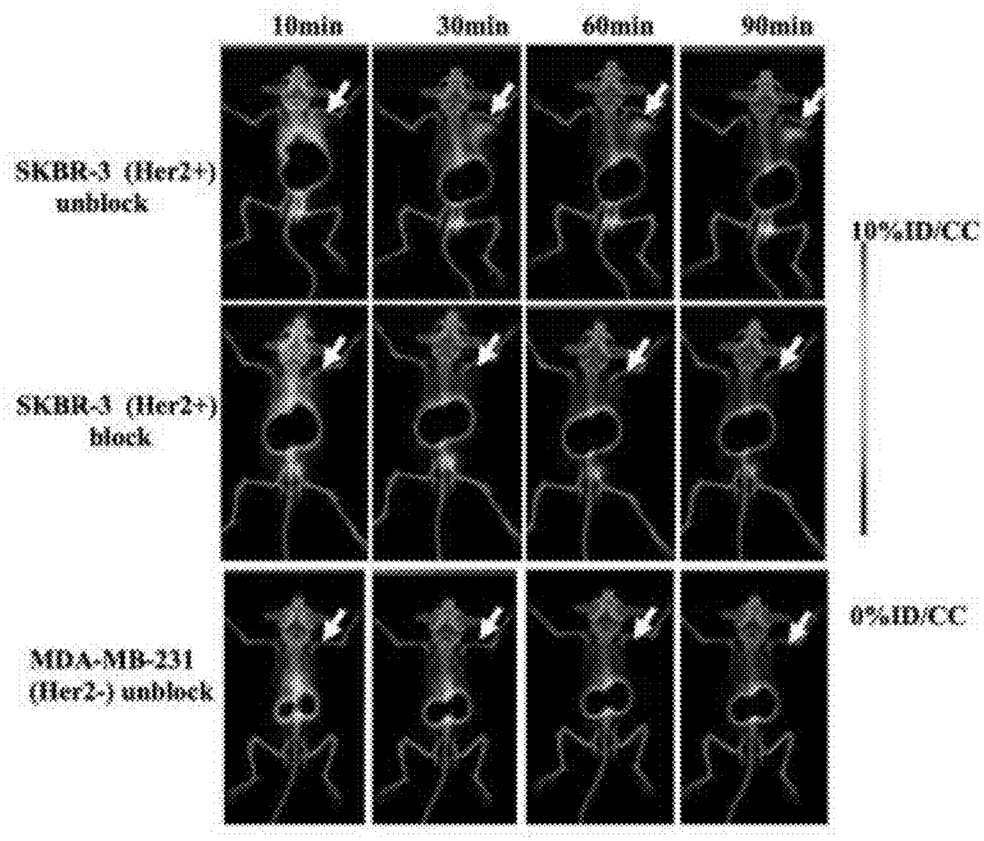
FIGS. 7*a* and 7*b* show a tumor imaging diagram of a PET/CT imaging of a $^{68}$Ga-BindHer molecular probe in a transplant model of a nude mouse with a breast cancer in Example 8, showing specific binding to Her2.
Figure 7B:
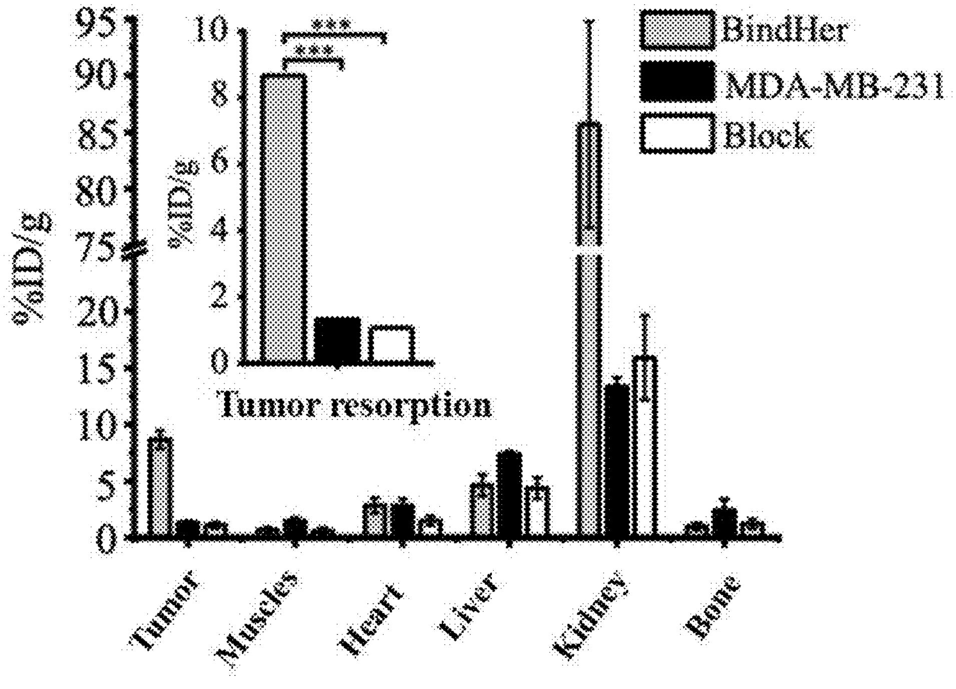

The results are shown in FIGS. 7*a* and 7*b*. FIG. 7*a* show images developed at 10 min, 30 min, 60 min, and 90 min after the injection of $^{68}$Ga-BindHer in the process of dynamic imaging of animals with the PET/CT imaging instrument. Compared with the blocking group and the Her2-negative group, the targeted absorption can be observed at the tumor site (see radioactive concentration) (indicated by an arrow), with significant difference ($P<0.01$) as shown in FIG. 7*b*.

Example 9

The preparation of a $^{18}$F-BindHer molecular probe and effects specific binding to Her2 tumor exhibited in PET/CT imaging in a nude mouse with a HER2-positive cell transplant tumor are described in this example.

1. Preparation of $^{18}$F-BindHer Molecular Probe:

100 μL of precursor protein BindHer-NOTA (with a precursor protein concentration of 2 mg/mL, and a buffer was 0.1 M, pH 4.0 sodium acetate solution) was taken and added with 7.5 μL of 2 mM aluminum chloride solution (a molar ratio of protein to aluminum chloride=1:0.6), and mixed well. Then, 20 μL of $^{18}$F (370 MBq) was added, and an equal volume of absolute ethanol was added, mixed and then reacted at 100° C. for 15 min. 10 column volumes were equilibrated with PBS and purified with a NAP-5 column (a maximum loading volume of 500 μL), then the above reaction mixture was allowed to pass through the column, eluted with PBS, and the eluate was collected. The concentration of the collected sample was detected using Nanodrop, and its radiological purity was detected to be 93.2±0.62% by using iTLC.

2. In Vivo PET/CT Imaging

An animal tumor model was established in the same manner as described in Example 5. 10 μg (about 1.5 MBq/mouse, diluted to 100 μL with normal saline) of $^{18}$F-BindHer molecular probe was injected into the breast cancer-bearing mice through the tail veins, and a PET/CT imaging instrument was used for dynamic imaging of the animals after injecting a developer.

Figure 8A:
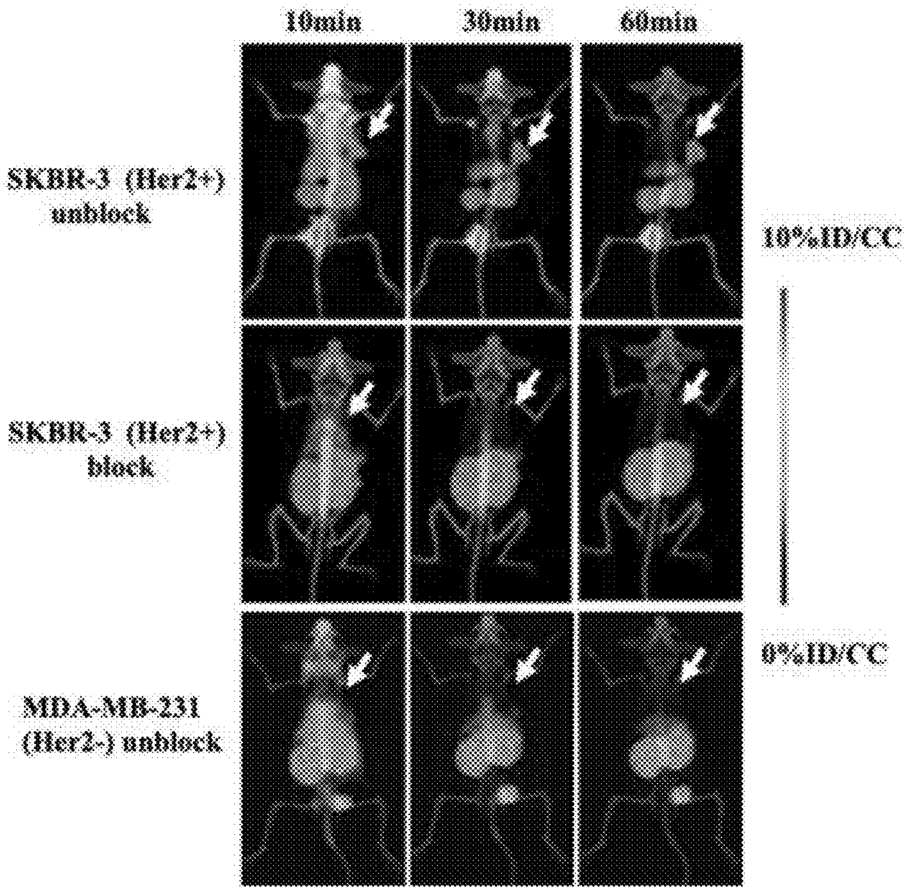
FIGS. 8*a* and 8*b* show a tumor imaging diagram of a PET/CT imaging of a $^{18}$F-BindHer molecular probe in a transplant model of a nude mouse with a breast cancer in Example 8, showing specific binding to Her2.
Figure 8B:
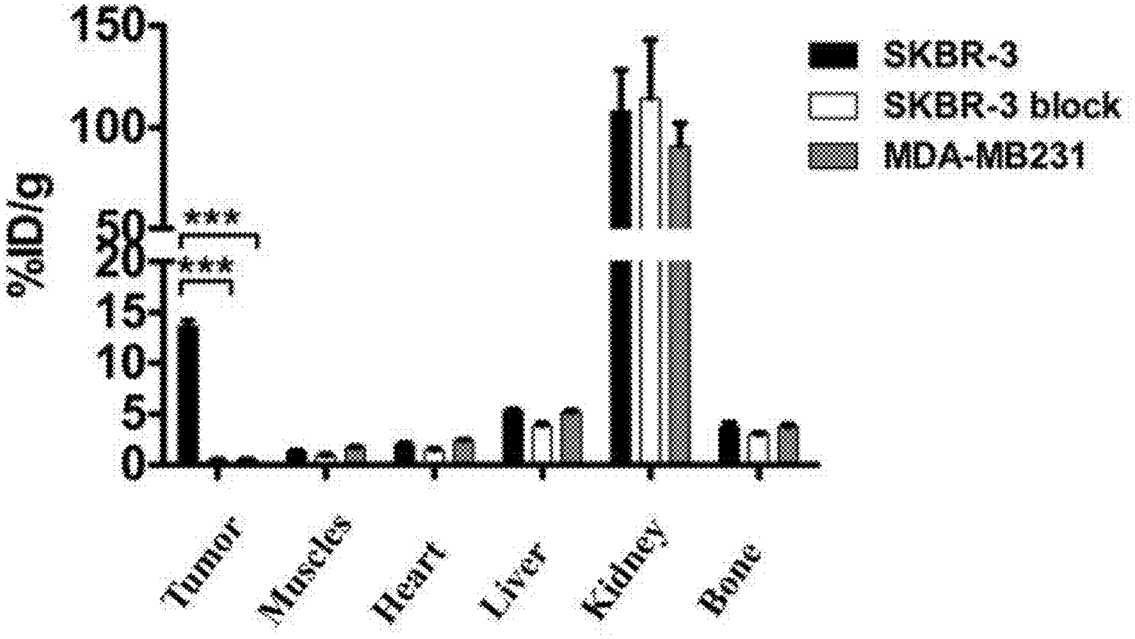

The results are shown in FIGS. 8*a* and 8*b*. As shown in FIG. 8*a*, PET/CT imaging of breast cancer-bearing mice indicates that the binding to a Her2-positive tumor can be observed in 10 min after the injection of $^{18}$F-BindHer molecular probe, a clear image may be obtained in 0.5 h; and compared with the blocking group and the Her2-negative group, obvious concentration and targeted absorption can be observed at the tumor site (see radioactive concentration) (indicated by an arrow), with significant difference ($P<0.01$) as shown in FIG. 8*b*.

The described examples are some embodiments, rather than all examples, of the present disclosure. The detailed description of examples of the present disclosure is not intended to limit the scope of the present disclosure, but merely indicating selected examples of the present disclosure. Based on the examples of the present disclosure, all other examples derived by those skilled in the art without paying creative efforts shall fall within the protection scope of the present disclosure.

What is claimed is:

1. A binding protein targeting HER2, wherein amino acid sequence of the binding protein is as set forth in SEQ ID NO: 1.

* * * * *